United States Patent
Rubinsky et al.

(10) Patent No.: US 10,939,949 B2
(45) Date of Patent: Mar. 9, 2021

(54) METHODS, SYSTEMS, AND APPARATUSES FOR TISSUE ABLATION USING PULSE SHAPE DESIGNS

(71) Applicants: INTER SCIENCE GMBH, Gisikon (CH); RM2 TECHNOLOGY LLC, Rancho Mission Viejo, CA (US)

(72) Inventors: Boris Rubinsky, El Cerrito, CA (US); Paul Mikus, Coto de Caza, CA (US); Liel Rubinsky, El Cerrito, CA (US); Michael Klaus Stehling, Rödermark (DE); Enric Günther, Hattersheim (DE)

(73) Assignees: INTER SCIENCE GMBH, Gisikon (CH); RM2 TECHNOLOGY LLC, Rancho Mission Viejo, CA (US)

( * ) Notice: Subject to any disclaimer, the term of this patent is extended or adjusted under 35 U.S.C. 154(b) by 550 days.

(21) Appl. No.: 15/570,914

(22) PCT Filed: May 13, 2015

(86) PCT No.: PCT/US2015/030628
§ 371 (c)(1),
(2) Date: Oct. 31, 2017

(87) PCT Pub. No.: WO2016/178697
PCT Pub. Date: Nov. 10, 2016

(65) Prior Publication Data
US 2018/0193082 A1    Jul. 12, 2018

Related U.S. Application Data

(60) Provisional application No. 62/155,623, filed on May 1, 2015.

(51) Int. Cl.
*A61B 18/12*    (2006.01)
*A61B 18/14*    (2006.01)
(Continued)

(52) U.S. Cl.
CPC ...... *A61B 18/1206* (2013.01); *A61B 18/1402* (2013.01); *A61N 1/205* (2013.01);
(Continued)

(58) Field of Classification Search
CPC .... A61N 1/0412; A61N 1/0428; A61N 1/325; A61N 1/327; A61B 2018/00613
See application file for complete search history.

(56) References Cited

U.S. PATENT DOCUMENTS 5,389,069 A    2/1995 Weaver et al.
5,468,223 A    11/1995 Mir
(Continued)

FOREIGN PATENT DOCUMENTS

EP    2425871 A2    3/2012
EP    1696812 B1    7/2015
(Continued)

OTHER PUBLICATIONS

International Search Report and Written Opinion received for PCT US2015/030628 dated Jan. 15, 2016.
(Continued)

*Primary Examiner* — Ronald Hupczey, Jr.
(74) *Attorney, Agent, or Firm* — Dorsey & Whitney LLP

(57) ABSTRACT

Example methods and apparatuses are disclosed for providing tissue ablation through electrolysis, electroporation, or a combination thereof. A way to deliver the combination through a pulse that has an element of gradual decay and can thereby reduce both muscle contraction and electric breakdown discharge at the electrodes is disclosed. The apparatus disclosed may include an electrode, a power supply, and a controller. The controller may control a charge applied to the electrode to induce a direct current through a treatment site to produce electrolysis products and a voltage to produce electroporation. The duration and magnitude of the charge
(Continued)

applied may determine the dose of the products and the degree of the permeabilization of cells in the treatment site.

12 Claims, 9 Drawing Sheets

(51) Int. Cl.
*A61N 1/20* (2006.01)
*A61B 18/00* (2006.01)
*A61B 5/145* (2006.01)
*A61N 1/32* (2006.01)

(52) U.S. Cl.
CPC .......... *A61N 1/327* (2013.01); *A61B 5/14539* (2013.01); *A61B 2018/00577* (2013.01); *A61B 2018/00613* (2013.01); *A61B 2018/00827* (2013.01); *A61B 2018/00994* (2013.01); *A61B 2018/1266* (2013.01); *A61B 2018/1472* (2013.01)

(56) References Cited

U.S. PATENT DOCUMENTS

| | | | |
|---|---|---|---|
| 5,911,223 | A | 6/1999 | Weaver et al. |
| 6,300,108 | B1 | 10/2001 | Rubinsky et al. |
| 6,366,808 | B1 | 4/2002 | Schroeppel et al. |
| 6,403,348 | B1 | 6/2002 | Rubinsky et al. |
| 7,113,821 | B1* | 9/2006 | Sun .................. A61B 5/14514 424/489 |
| 7,344,533 | B2 | 3/2008 | Pearson et al. |
| 7,680,543 | B2* | 3/2010 | Azure ............... A61B 18/1477 606/41 |
| 7,718,409 | B2 | 5/2010 | Rubinsky et al. |
| 7,955,827 | B2 | 6/2011 | Rubinsky et al. |
| 8,048,067 | B2* | 11/2011 | Davalos ............ A61B 18/1233 606/32 |
| 8,145,316 | B2 | 3/2012 | Deem et al. |
| 8,282,631 | B2 | 10/2012 | Davalos et al. |
| 8,926,606 | B2 | 1/2015 | Davalos et al. |
| 9,005,189 | B2 | 4/2015 | Davalos et al. |
| 9,283,051 | B2 | 3/2016 | Garcia et al. |
| 9,700,368 | B2 | 7/2017 | Callas et al. |
| 9,901,735 | B1 | 2/2018 | Lee et al. |
| 10,154,873 | B2 | 12/2018 | Rubinsky et al. |
| 10,390,874 | B2 | 8/2019 | Rubinsky et al. |
| 2001/0021868 | A1 | 9/2001 | Herbst et al. |
| 2002/0010491 | A1 | 1/2002 | Schoenbach et al. |
| 2003/0042134 | A1 | 3/2003 | Tremblay et al. |
| 2004/0213698 | A1 | 10/2004 | Tennakoon et al. |
| 2006/0116663 | A1 | 6/2006 | Joshi et al. |
| 2008/0167650 | A1 | 7/2008 | Joshi et al. |
| 2009/0287208 | A1 | 11/2009 | Rosemberg |
| 2010/0030211 | A1 | 2/2010 | Davalos et al. |
| 2010/0036446 | A9 | 2/2010 | Auge et al. |
| 2010/0168646 | A1 | 7/2010 | Greenbaum et al. |
| 2010/0183745 | A1 | 7/2010 | Rossi et al. |
| 2012/0059255 | A1 | 3/2012 | Paul et al. |
| 2012/0071874 | A1 | 3/2012 | Davalos et al. |
| 2012/0130369 | A1 | 5/2012 | Cadossi et al. |
| 2012/0150173 | A1 | 6/2012 | Joshi et al. |
| 2012/0220998 | A1 | 8/2012 | Long et al. |
| 2013/0218157 | A1 | 8/2013 | Callas et al. |
| 2014/0066913 | A1* | 3/2014 | Sherman ............ A61B 18/1492 606/20 |
| 2014/0316485 | A1 | 10/2014 | Ackermann et al. |
| 2016/0184003 | A1 | 6/2016 | Srimathveeravalli et al. |
| 2016/0287867 | A1 | 10/2016 | Rubinsky et al. |
| 2016/0296269 | A1 | 10/2016 | Rubinsky et al. |
| 2019/0117291 | A1 | 4/2019 | Rubinsky et al. |
| 2019/0357960 | A1 | 11/2019 | Rubinsky et al. |

FOREIGN PATENT DOCUMENTS

| | | |
|---|---|---|
| WO | 03103521 A1 | 12/2003 |
| WO | 2007070637 A2 | 6/2007 |
| WO | 2015021113 A1 | 2/2015 |
| WO | 2015073877 A1 | 5/2015 |
| WO | 2015073885 A1 | 5/2015 |
| WO | 2016178697 A1 | 11/2016 |

OTHER PUBLICATIONS

Ivorra, et al., "Electric Field Modulation in Tissue Electroporation With Electrolytic and Non-Electrolytic Additives", Bioelectrochemistry 70, Feb. 2007, pp. 551-560.

Ivorra, et al., "In Vivo Electrical Impedance Measurements During and After Electroporation of Rat Liver", Bioelectrochemistry 70, Oct. 2006, pp. 287-295.

Office Action for CN Application No. 201580080597,8, dated May 7, 2020.

Mir, et al., "Mechanisms of Electrochemotherapy", Advanced Drug Delivery Reviews, vol. 35, No. 1, Jan. 1, 1999, pp. 107-118, XP055754391, Amsterdam, NL.

* cited by examiner

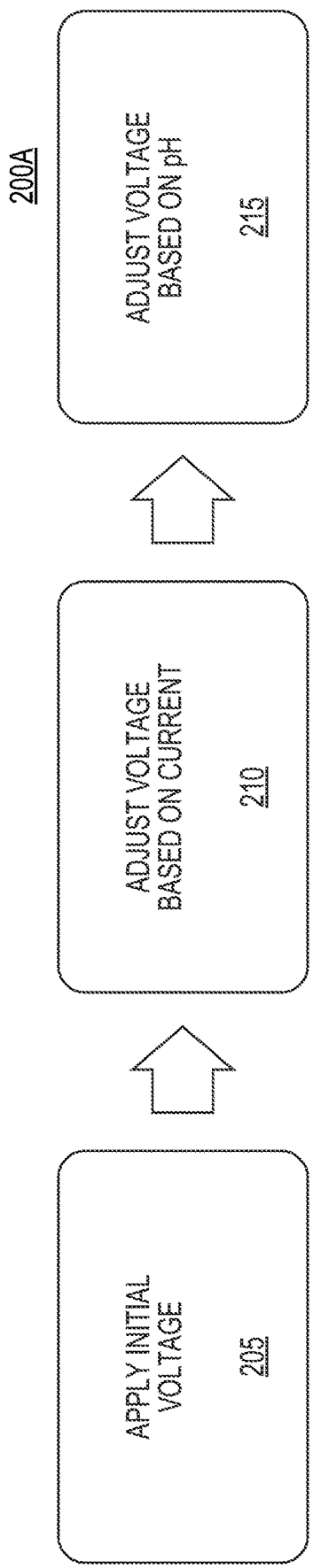
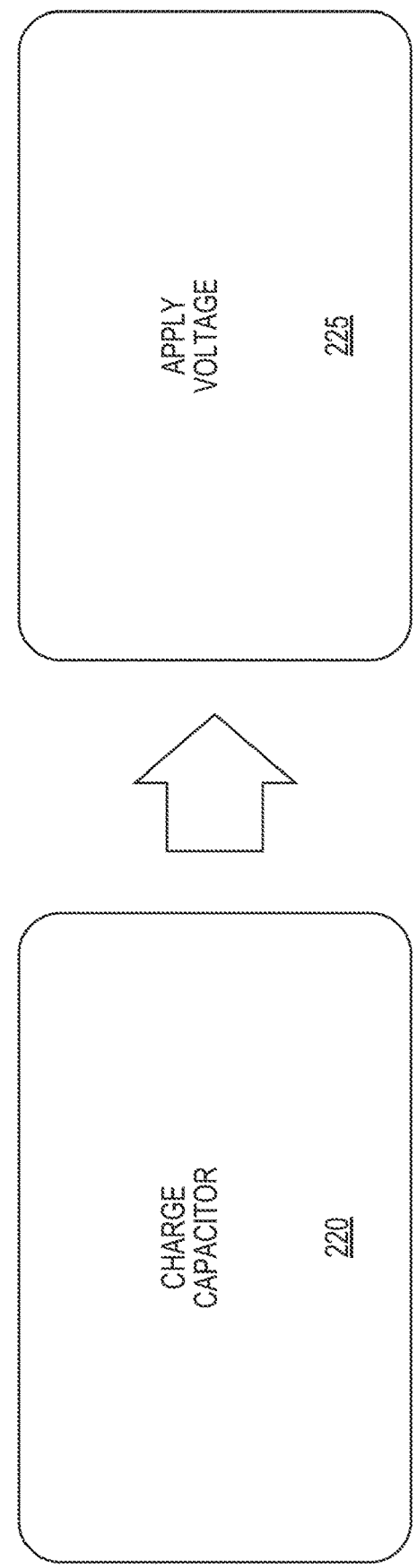
Fig. 2A
Fig. 2B

| FIELD V/cm (ACTUAL APPLIED VOLTAGE, (V)) | PULSE LENGTH, ms | CHARGE DELIVERED, NORMALIZED | INTERVAL BETWEEN PULSES, (ms) | NUMBER OF PULSES | TOTAL TIME OF CELLS IN CUVETTES (S) | %SURVIVAL TRYPAN BLUE | pH |
|---|---|---|---|---|---|---|---|
| 2500 (500) | 1 | 1.25 | | 1 | 0.001 | 32+/-5 | 9.6+/-0.1 |
| 2000 (400) | 1.5 | 1.5 | | 1 | 0.0015 | 23+/-14 | 9.05+/-0.15 |
| 1500 (300) | 3 | 2.25 | | 1 | 0.003 | 24+/-10 | 9.45+/-0.15 |
| 1000 (200) | 6 | 3 | | 1 | 0.006 | 10+/-5 | 10.45+/-0.15 |
| 500 (100) | 24 | 6 | | 1 | 0.024 | 22+/-18 | 9.65+/-0.5 |

Fig. 6

METHODS, SYSTEMS, AND APPARATUSES FOR TISSUE ABLATION USING PULSE SHAPE DESIGNS

RELATED APPLICATIONS

This application is a U.S. National Stage filing under 35 U.S.C. § 371 of PCT Application No. PCT/US2015/030628, filed May 13, 2015, which claims priority to U.S. Provisional Application No. 62/155,623 filed May 1, 2015, which applications are incorporated herein by reference, in their entirety, for any purpose.

BACKGROUND

Electrolysis has been used for minimally invasive tissue ablation since the early 1800's. The process of electrolysis occurs at the electrode surfaces for electrodes submerged in an ionic conducting media. New chemical species are generated at the interface of the electrodes as a result of the electric potential driven transfer between electrons and ions or atoms. The various chemical species produced near the electrodes diffuse away in a process driven by differences in electrochemical potential. In physiological solutions these chemical reactions also yield changes in pH, resulting in an acidic region near the anode and a basic region near the cathode. Tissue ablation is driven by two factors: a cytotoxic environment developing due to local changes in pH, as well as the presence of some of the new chemical species formed during electrolysis. Electrolysis is a chemical ablation mechanism, and the extent of ablation is a function of the concentration of the chemical species and the exposure time to these chemicals. The total amount of electrolytic products generated during electrolysis is related to the charge delivered during the process, and therefore the total charge is used as a quantitative measure for the extent of electrolysis.

Over the last two decades, substantial research has been done on tissue ablation by electrolysis, including cell and animal experiments, mathematical modeling, and clinical work. In the contemporary literature, electrolytic ablation is sometimes referred to as Electro-Chemical Therapy (EChT). Electrolytic ablation has been shown to exhibit several unique attributes. First, due to the chemical nature of the ablation process, the diffusion of chemical species in the tissue and the rate of chemical reactions dominate the time scale of the procedure. Second, the chemical products at the anode differ from those formed at the cathode, thus resulting in distinct mechanisms of ablation. Finally, electro-osmotic forces drive the migration of water from the anode to the cathode, further magnifying the contrasting physiological effects at the electrode surfaces. From an operational standpoint, electrolysis may use very low voltages and currents, providing advantages relative to other ablation techniques, e.g. reduced instrumentation complexity. It is, however, a lengthy procedure, controlled by the process of diffusion and the need for high concentrations of electrolytically-produced ablative chemical species.

Electroporation also harnesses an electricity-induced phenomenon; it differs from electrolysis by employing a different set of biophysical principles. The bioelectric phenomenon of electroporation is characterized by the permeabilization of the cell membrane through the application of very brief, high-magnitude electric field pulses. The extent of membrane permeabilization is a function of the electric field strength. Electroporation can be used to produce reversible pores in the lipid bilayer, allowing for the introduction of molecules such as genes and drugs into cells. The electric parameters, however, can be designed to produce irreversible defects, resulting in a cell membrane that does not reseal after the field is removed. Reversible electroporation techniques have been combined with anticancer drugs such as bleomycin to target cancerous tissues for successful clinical use in the field of electrochemotherapy. Reversible electroporation is also used in other medical and biotechnological applications, including transfection and introduction of molecules such as siRNA into cells that survive the permeabilization process. Electroporation specifically targets the cell membrane through the application of an electric field that develops instantaneously.

SUMMARY

An example method for tissue ablation according to an embodiment of the disclosure may include delivering a pulse of a current or a voltage to a treatment site, wherein a magnitude and a duration of the pulse is selected to induce electroporation at the treatment site, and wherein the duration of the pulse is further selected to produce an amount of electrolytic products at the treatment site.

Another example method for tissue ablation according to an embodiment of the disclosure may include applying a pulse of a voltage or a current to a treatment site with an electrode; receiving a current measurement from the treatment site; and adjusting a magnitude of the pulse to the treatment site with a controller based on the current measurement, wherein the current measurement may be indicative of electroporation at the treatment site, and the magnitude of the pulse may be adjusted to induce electroporation at the treatment site.

A further example method for tissue ablation according to an embodiment of the disclosure may include charging a capacitance to an initial voltage with a power supply, and discharging the capacitance through a resistance and an electrode to provide a pulse to a treatment site, wherein the pulse comprises a voltage having an exponential decay defined by a time constant.

An example of an apparatus for tissue ablation according to an embodiment of the disclosure may include an electrode that may be configured to provide a pulse of a voltage or a current to a treatment site, and a controller coupled to the electrode, the controller may be configured to provide an electronic signal to the electrode, wherein the electronic signal may determine a rising edge, a plateau, and a falling edge of the pulse, wherein the rising edge, plateau, and falling edge of the pulse may be configured to induce at least one of electrolysis and electroporation at the treatment site.

BRIEF DESCRIPTION OF THE DRAWINGS

The foregoing and other features of the present disclosure will become more fully apparent from the following description and appended claims, taken in conjunction with the accompanying drawings. Understanding that these drawings depict only several examples in accordance with the disclosure and are, therefore, not to be considered limiting of its scope, the disclosure will be described with additional specificity and detail through use of the accompanying drawings, in which

FIG. 2A is a flow chart illustrating a method according to an embodiment of the disclosure.

FIG. 2B is a flow chart illustrating a method according to an embodiment of the disclosure.

FIG. 6 is a table of experimental results according to an illustrative example according to an embodiment of the disclosure.

DETAILED DESCRIPTION

Figure 1:
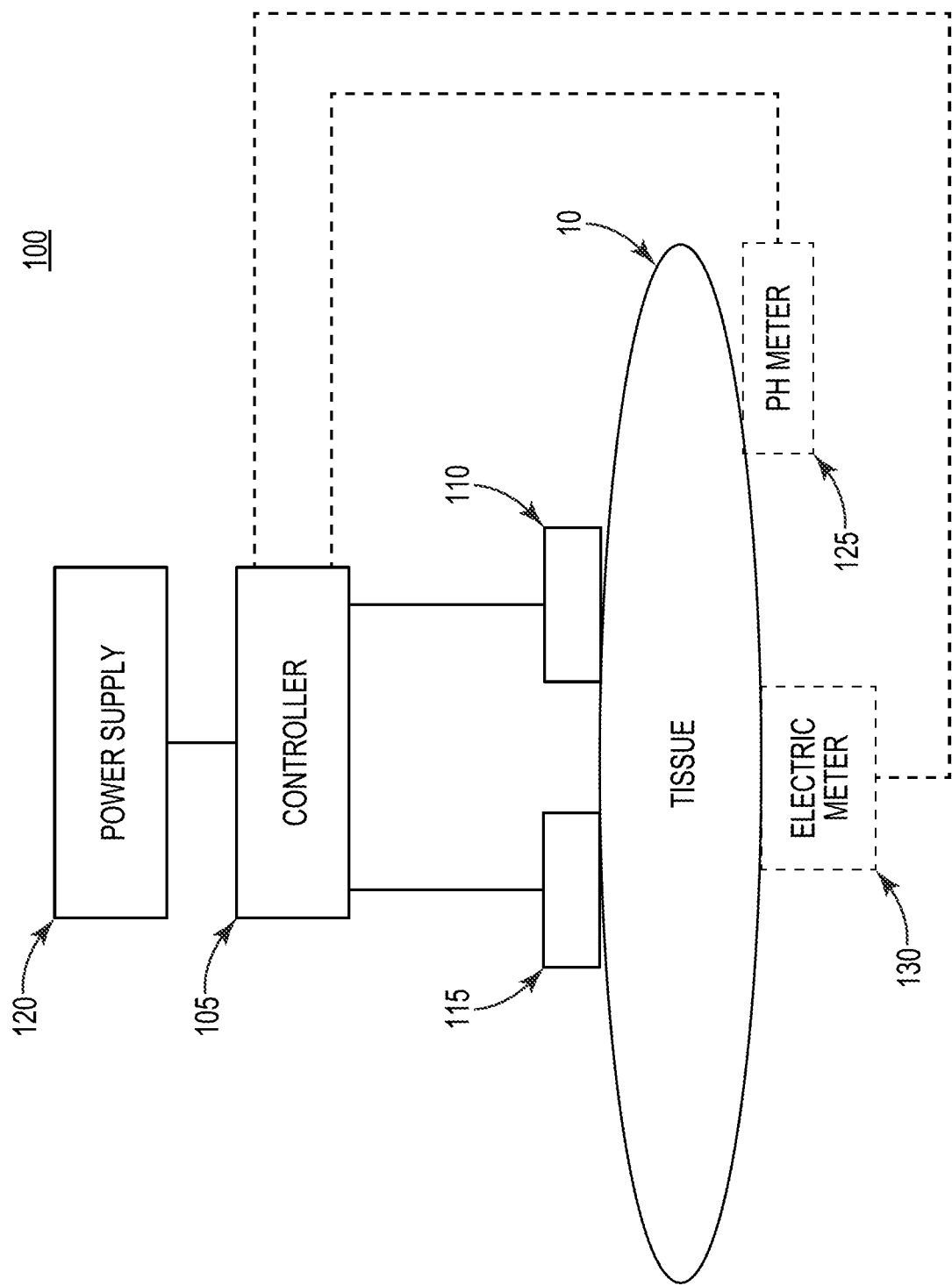
FIG. 1 is a schematic illustration of an electrolysis system according to an embodiment of the disclosure.

Certain details are set forth below to provide a sufficient understanding of embodiments of the disclosure. However, it will be clear to one skilled in the art that embodiments of the disclosure may be practiced without these particular details. Moreover, the particular embodiments of the present disclosure described herein are provided by way of example and should not be used to limit the scope of the invention to these particular embodiments. In other instances, well-known materials, components, processes, controller components, software, circuitry, timing diagrams, and/or anatomy have not been described or shown in detail in order to avoid unnecessarily obscuring the embodiments.

This disclosure describes tissue ablation systems and methods that may utilize certain pulse designs and operation protocols that may advantageously allow for tissue ablation using the combined effect of electroporation with electrolysis. Combining electroporation with electrolysis may produce a substantial increase in the extent of tissue ablation as compared to the ablation produced by the same dose of electrolysis or electroporation separately. Without being bound by a particular theory, this phenomenon may be attributed to the electrolytically produced chemicals that may pass through a permeabilized cell membrane into the interior of the cell, thereby causing cell damage at much lower concentrations of electrolytic products than for intact cells. This mechanism of tissue ablation may be affected by the dose of chemical species produced by electrolysis at the electrodes, the process of electro-osmotic diffusion from the electrodes into tissue and the permeabilization of the cell membrane in the targeted tissue.

Moreover, electroporation had previously been performed using a series of short (e.g. on the order of nanoseconds to milliseconds) voltage or current square-like pulses. This repetitive pulsing may cause repetitive, with each pulse, muscle contractions in the tissue, which may be or become violent muscle contractions such that the technique would be required to be performed under general anesthesia with paralyzing drugs. Moreover the products of tissue electrolysis generated during the delivery of the pulses may cause the formation of a gas layer around the electrodes which for square like pulse shapes yield ionization of the gases and a violent and uncontrollable electric discharge across the gas layer. Moreover, the repetitive pulsing for short times at high magnitudes (e.g. over 90 pulses at 1500V/cm) may cause mechanical stress in the tissue, which may be severe and could damage delicate tissues such as prostate, brain, or bone. Pulse designs and operation protocols are described herein which may reduce these undesirable effects. For example, application of a single voltage or current pulse that may be of a longer (e.g. on the order of milliseconds to seconds to minutes) duration but a lower voltage or current, and with a gradually decaying form, e.g. exponential decay may advantageously reduce or prevent the violent muscle contractions seen previously, while avoiding the electric discharge and allowing the time necessary for electrolysis products to diffuse into tissue to be effective in enhancing the tissue ablation.

Electrolysis generally refers to a process of inducing a chemical reaction that involves passing a direct current through an ionic solution via two electrodes. Electrolysis may facilitate the removal and/or addition of electrons from atoms and/or ions, which may lead to the formation of new products. For example, by passing a DC current through a saline solution ($NaCl$ and $H_2O$), hypochlorous acid ($HClO$) may be formed. The products formed may be based, at least in part, on the ionic composition of the solution, and/or its pH. The amount of electrolysis products formed may be based at least in part on the magnitude of the current and/or the duration the current is applied. The current may be generated by coupling a power source to the electrodes. Examples of power sources may include, but are not limited to, one or more, electrical network, batteries, a computer (e.g., coupled via universal serial bus (USB) cable), a solar cell, and combinations thereof.

In some embodiments of relevance to this patent, electrolysis may be used in combination with electroporation for inducing cell death in tissue. The combination treatment may be more effective at ablation and/or sterilization than the individual treatments used alone. The combination of electrolysis with electroporation in use for tissue ablation may generally be referred to as E2 herein.

Figure 1A:
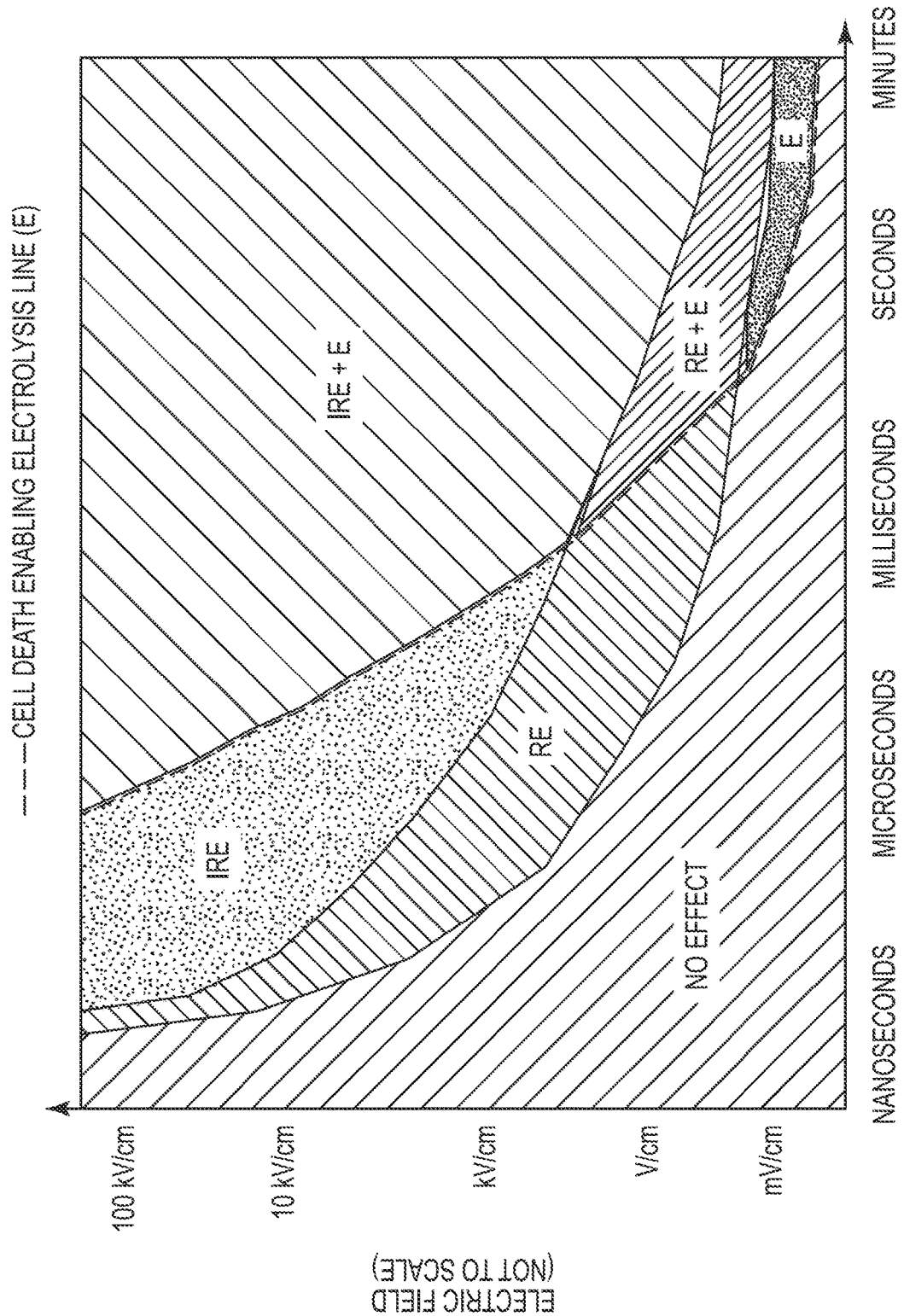
FIG. 1A is a schematic illustration of various domains for electroporation and electrolysis, with respect to their effect on tissue and cell ablation, according to an embodiment of the disclosure.

FIG. 1A is a schematic illustration of various domains for electroporation and electrolysis. The illustration shown in FIG. 1A is given as electric field strength versus time. While FIG. 1A is provided as an example of a typical curve, its characteristics (e.g., slope) may change with cell type. The values given on the axis are typical to mammalian cells. The time range for irreversible electroporation may be from nanoseconds to minutes and the voltage range may be from several hundred V/cm (200 V/cm) to 100 V/cm. For reversible electroporation that voltage range may be from 50 V/cm to several hundred V/cm (500 V/cm) and the time range may also be from nanoseconds to several minutes. Electrolysis may occur when current flows from electrodes to tissue (electrons to and from ions) and/or when the voltage exceeds a certain threshold prescribed by the electrochemical potential of the electrodes in relation to the solution. This threshold value may depend on the electrode material, composition of the solution, pH, and/or temperature. Typical values may be several volts, for example from 0.01 V to 10 V. In FIG. A1, the curve that displays values in which electrolysis products cause cell death may include multiple regions. That curve may include regions in which cell death may be caused by electrolysis alone, by combination of reversible electroporation and electrolysis, and/or combination of irreversible electroporation and electrolysis. We define the domain above the electrolysis cell death curve for electric fields above the reversible electroporation curve and above the irreversible electroporation curve E2. Confirming if a tissue ablation protocol is included in the E2 region or not may be done by determining if cell death in that region occurs even when the products of electrolysis are eliminated, while the other parameters remain unchanged. The diagram illustrated in FIG. 1A is schematic. However, it illustrates that the minimal time of exposure required for cell death with involvement of electrolysis may increase in the following order: a) combination used from irreversible electroporation with electrolysis to b) reversible electroporation with electrolysis to c) electrolysis alone. As shown in FIG. 1A, the electrolytic involvement cell death curve may only have a lower limit, since electrolysis may occur in the presence of a process that involves transfer of electrons to ions, but may not always cause cell death. Typical times for IRE+E are single microseconds (e.g., approximately 0.1 microsecond-1 microsecond) and for RE+E are several tens of microseconds (e.g., 10 microseconds) and for E are seconds (e.g., 1 sec).

For a given electric field strength, the electric field applied for over a threshold time may generate sufficient electrolysis to enable cell death to occur. The threshold amount of time required may vary based on the electric field strength used. Accordingly, as seen in FIG. 1A, there may be at least five domains—a region of reversible electroporation only (RE), a region of irreversible electroporation (IRE) only, a region of reversible electroporation plus electrolysis (RE+E), a region of irreversible electroporation plus electrolysis (IRE+E), and a region of electrolysis without electroporation (E). As used herein, the regions of IRE+E and RE+E are referred to as E2. Tissue ablation may be performed using the desired techniques (e.g. IRE, RE, E, IRE+E, or RE+E) by selecting a field strength and time associated with the domain of interest.

An example method of tissue ablation through the delivery of products of electrolysis to a targeted volume of tissue, in combination with the permeabilizing of the cell membrane of the cells in targeted volume of tissue may include, bringing electrode needles to the proximity of the interior and/or exterior of the targeted volume of tissue, delivering electric potential to the electrodes to generate electric fields that permeabilize the cell membrane in the targeted volume of tissue, delivering electric current to the electrodes for generating the electrolytic products at the electrodes at an amount sufficient to ablate permeabilized cells in the targeted volume of tissue, and electro-osmotic diffusion of the electrolytic products throughout the targeted volume of tissue. Permeabilization and production of electrolytic products may be done in any sequence that achieves the goal of bringing the products to the cells in the targeted volume of tissue and at the same time permeabilizing these cells, such as permeabilizing the volume of cells in tissue first and generating the required amount of products of electrolysis next, generating the amount of electrolytic products first and permeabilizing the cell membrane next, permeabilizing the volume of cells first, generating the required products of electrolysis next and then permeabilizing the volume of cells again, simultaneously permeabilizing the cell membrane and producing the products of electrolysis, or any combination of these. The electrodes brought to the proximity of the tissue can serve for both electrolysis and electroporation or some of the electrodes may be dedicated for electroporation and others for electrolysis.

FIG. 1 is a schematic illustration of a multimodality electrolysis system 100 according to an embodiment of the disclosure. The multimodality electrolysis system 100 may be capable of performing electrolysis and at least one other treatment, such as cellular permeabilization treatment. Although the system 100 in FIG. 1 is shown on the surface of a tissue 10, the system 100 may be configured to be used inside tissue 10, proximate tissue 10, and/or in a cavity formed by tissue 10 in some embodiments. In some embodiments, the system 100 may include a controller 105 coupled to an electrolysis device 110 and a cellular permeabilization device 115. The cellular permeabilization device 115 may also be referred to as a cellular electroporation device. Although shown as separate devices in some embodiments the electrolysis device 110 and the cellular permeabilization device 115 may be the same device. The devices 110, 115 may be placed proximate to a treatment site on tissue 10, either in the interior and/or the exterior of the treatment site The controller 105 may control the timing, strength, and duration of treatments provided by the devices 110, 115. The controller 105 may, for example, be programmed to provide an electronic signal to the devices 110, 115. The electronic signal may be indicative of a dose of treatment, for example, a dose of electrolysis products. The electronic signal may control the timing and magnitude of a current generated by the electrolysis device 110 and/or the cellular permeabilization device 115, which may be implemented as an electroporation device. This may allow a user to customize treatment of the tissue 10. In some embodiments, the controller is coupled to a power supply 120. In some embodiments, the power supply 120 may be included in device 110 and/or device 115. In some embodiments, the power supply 120 is integrated with controller 105.

Although shown as a separate component coupled to the devices 110, 115, in some embodiments, the controller 105 may be integrated into one or both devices 110, 115 and/or packaged together with one or both devices 110, 115. In some embodiments, the controller 105 may include a programmable chip coupled to the devices 110, 115. Some embodiments, the controller 105 may be implemented using a computing device (not shown) and be remotely coupled to the devices 110, 115. The computing device may be implemented using, for example, a desktop, laptop, server, handheld device, a personal computer, a tablet computer, and/or a smart phone. In some examples, the computing device may be integrated with and/or shared with another piece of medical equipment. The controller 105 may be coupled by a wire or communicate with the devices 110, 115 wirelessly. In some embodiments, two separate controllers may be used in system 100. Each controller may be coupled to one of the devices 110, 115.

In some embodiments, the controller 105 may be programmed to provide an electronic signal indicative of a dose of the electrolysis products and/or a permeability level of cells. The controller 105 may, for example, include such a program, or include one or more processing devices (e.g. processors) coupled to a memory encoded with executable instructions for electrolysis treatment and at least one other treatment, such as cellular permeabilization treatment.

The system 100 may further include one or more sensors for measurement of pH 125, electronic field strength or/and electric current 130, and/or other properties of the tissue 10. For example, the sensor may sense pH near the electrolysis device 110 and provide the pH value to the controller 105. The controller 105 may further be programmed to adjust an electronic signal provided to the electrolysis device 110 based on the pH near the device. A reservoir (not shown) may be provided for addition of compounds, such as buffers or other solutions, to the tissue to adjust the pH. In another example the pH sensor 125, may be inserted at the outer edge of the targeted volume of tissue to detect when the pH at the site has reached a desired level which may ensure the ablation of tissue at that site. This may be used as an indicator by the controller 105 to stop the electrolysis process. In another example the pH sensor 125, may be inserted at a particular site in tissue to detect when the pH at the site is reaching a potentially damaging value to avoid tissue damage at that site. This may be used as an indicator by the controller to stop the electrolysis process. In some examples the electric meter 130 may be set at a particular location in tissue to measure isoelectric field levels which may ensure that the cells at that location are permeabilized. The electric meter 130 may be implemented as an electrical conductivity meter.

In some embodiments, the electrolysis device 110 includes one or more electrodes for conducting a current through a solution. The solution may be native to the treatment site and/or it may be introduced to the treatment site. In some embodiments, the electrolysis device 110 includes an aqueous matrix in contact with the electrodes for placement proximate the treatment site. In some embodiments, the aqueous matrix may be a gel including a saline solution. In some embodiments, the electrolysis device 110 may include needle electrodes and/or a catheter for use within cavities and/or tissues.

The cellular permeabilization device 115 may perform reversible and/or irreversible permeabilization. In some embodiments, the cellular permeabilization device 115 is an electroporation device. The electroporation device may include one or more electrodes for conducting a current through a tissue for permeabilizing cells. The permeability of the cells and/or the reversibility of the permeabilization may be based, at least in part, on the magnitude of the local electric field in tissue and/or duration of the electroporation treatment. In some embodiments, the cellular permeabilization device 115 is a sonoporation device, which may use ultrasound for permeabilization. In some embodiments, the cellular permeabilization device 115 may implement another permeabilization method such as, but not limited to, cryosurgery, freezing, coldporation, heatporation, and chemoporation.

In some embodiments, electrolysis device 110 may be packaged with the cellular permeabilization device 115. In some embodiments, the electrolysis device 110 and cellular permeabilization device 115 may be a single device. For example, the electrodes for performing electrolysis may also be used for performing electroporation.

For example, the electrolysis device 110 and the cellular permeabilization device 115 may in some examples be implemented using a single device, e.g. a device including an electric field generator which may include a voltage or current supply. The controller 105 and/or the device combining electrolysis device 110 and 115 may provide one or more voltage or current pulses to the tissue 10 sufficient to have operation in the desired domain of electroporation and/or electrolysis.

In some examples, a single pulse of voltage and/or current may be provided to the tissue 10 and may cause both cell death through reversible or irreversible electroporation and cell death through electrolysis. It has been observed that a single pulse of voltage or current may be advantageous over multiple pulse examples in some situations, because the single pulse may, for example, reduce severe muscle contractions and/or sparking.

Figure 1B:
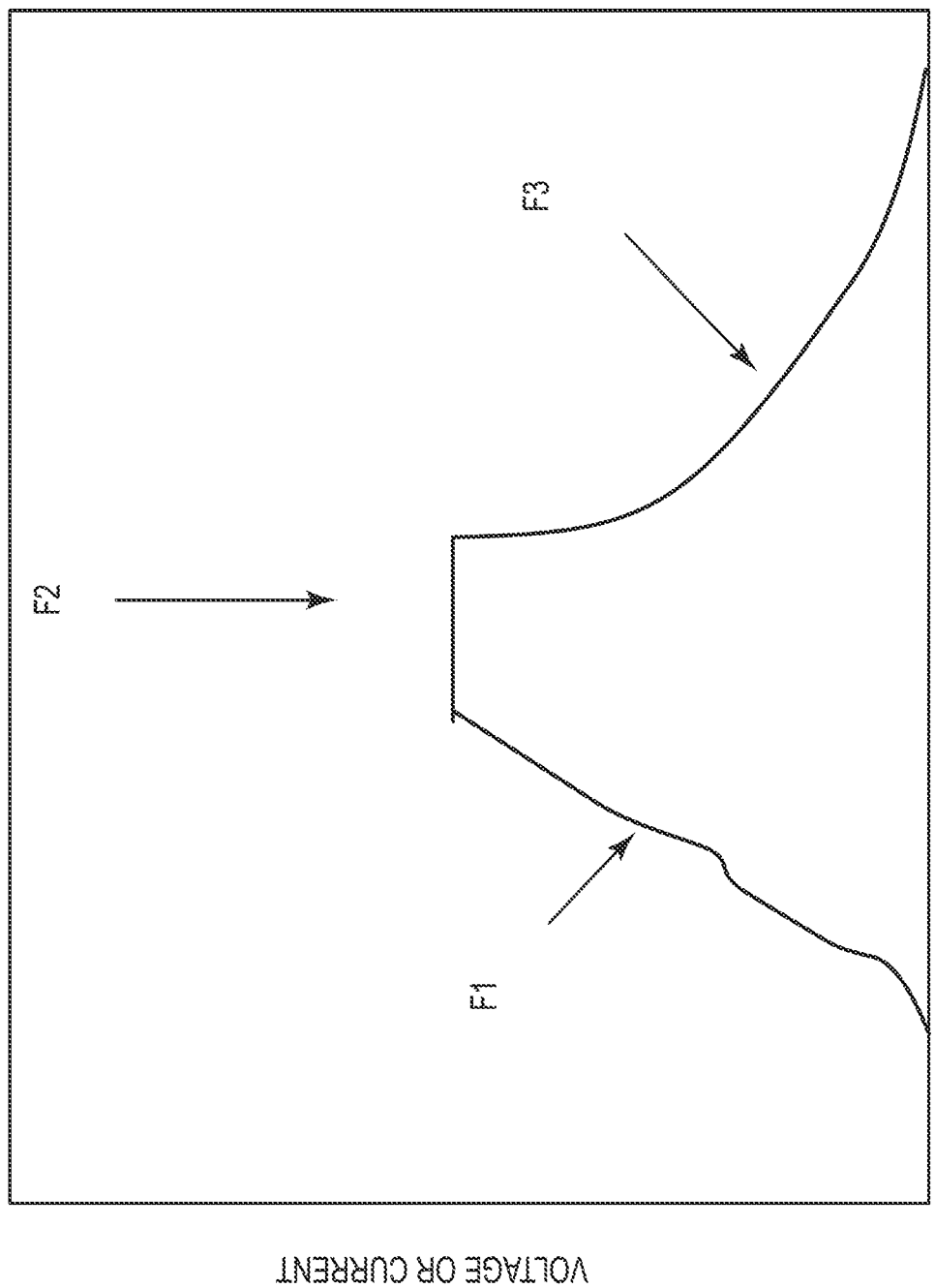
FIG. 1B is a schematic illustration of a pulse design in accordance with an example of the present disclosure.

FIG. 1B is a schematic illustration of a pulse design in accordance with an example of the present disclosure. The pulse shown in FIG. 1B may be applied by the device 110 and/or 115 in some examples, and may be specified by the controller 105 in some examples. Generally, the pulse may have three components—a rising edge, labeled F1, a plateau, labeled F2, and a falling edge, labeled F3. Use of a single pulse (as opposed to repeated pulses) during which electroporation and electrolysis may occur may be advantageous in some examples. The pulse may be of a variety of different shapes, including but not limited to an exponential decay, a square wave, a triangle wave and wave with a rising leading edge or falling trailing edge.

Generally, the rising edge F1 may rise to a voltage sufficient to induce reversible or irreversible electroporation electric fields throughout the targeted treated domain. Example values for reversible electroporation include, but are not limited to voltages above 100 V/cm and for irreversible electroporation, voltages above 400 V/cm, as shown in FIG. 1A. The rise may be between nanoseconds and seconds. The plateau portion F2 may last long enough that together with the rise time and decay time, it produces the desired electroporation effect. However, it may be desirable that the plateau portion F2 is short enough to eliminate the electric discharge across a gaseous layer that may develop near the electrodes. In some embodiments, the plateau may be infinitesimally small. The decaying edge F3 may decay so that the electric field across the electrolytic gas layer that may form near the electrodes is less than the ionization field of about 30,000 V/cm to avoid sparking, but provides an adequate voltage long enough to produce the desired products of electrolysis for tissue ablation. In some embodiments, the rising edge F1, plateau portion F2, and/or falling edge F3 of the pulse may be designed so that ablation occurs primarily or exclusively from electroporation rather than electrolysis.

Figure 1C:
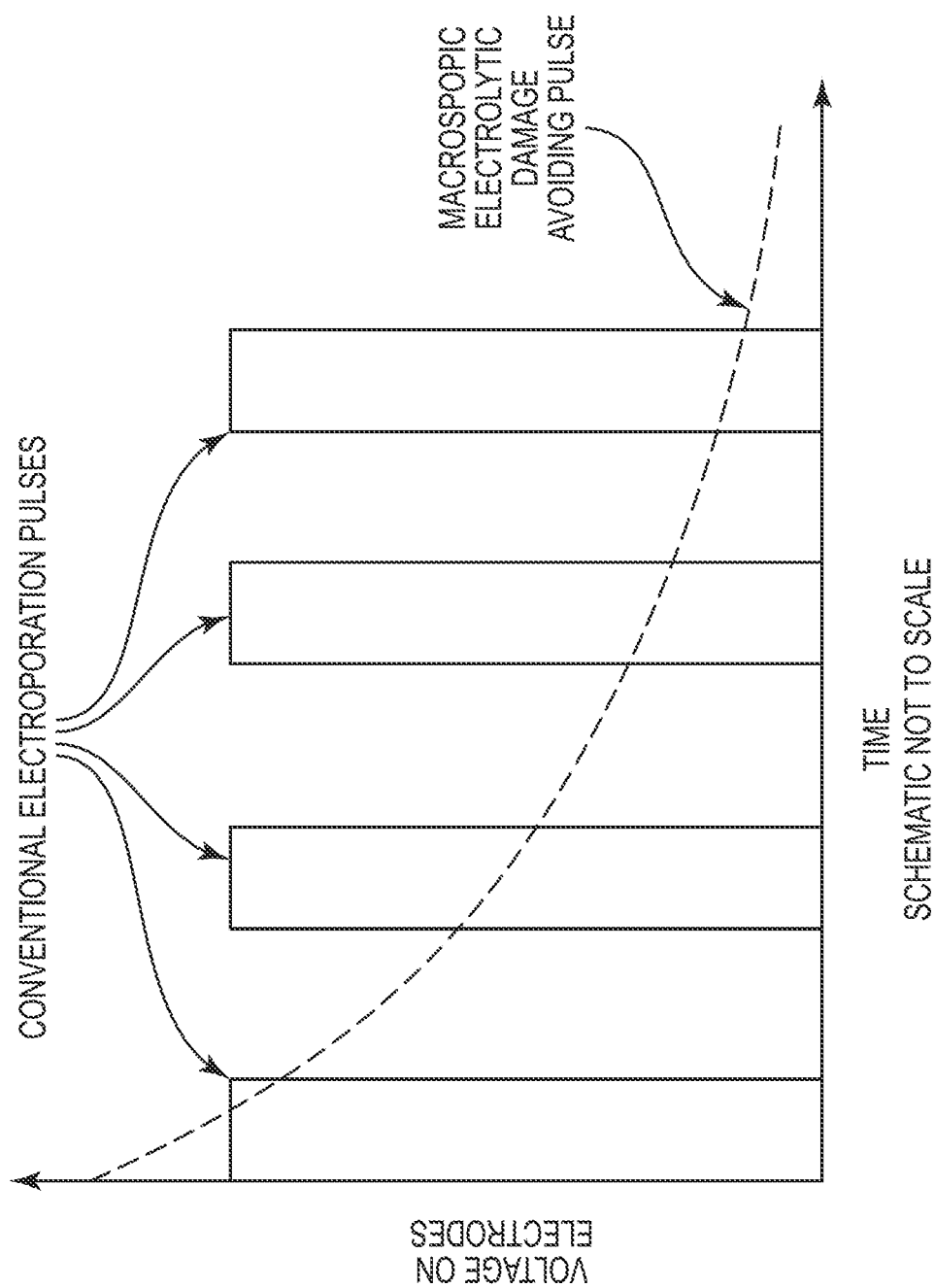
FIG. 1C is a schematic illustration showing a pulse design in accordance with examples described herein overlaid on a conventional pulse design.

FIG. 1C is a schematic illustration showing a pulse design in accordance with examples described herein overlaid on a conventional pulse design. As can be seen in FIG. 1C, a decaying edge of a pulse (which may have no or a negligible plateau and rising edge as seen in FIG. 1C) may have exponential decay. The pulse may have a magnitude which is instantaneously, or briefly, above the magnitude of a conventional electroporation pulse sequence. However, the exponentially decaying pulse decays from that higher value to avoid the electric discharge across the electrolytically formed gas layer and may provide an electric field for a longer period of time to generate electrolytic products in a sufficient quantity for tissue ablation. In some embodiments, the magnitude of the pulse and the exponential decay may be selected so that ablation occurs primarily or exclusively from electroporation rather than electrolysis.

In some embodiments, regardless of the IRE zone in which it is used, a decaying pulse may produce cell death with much less muscle contraction for the same zone of ablated region—e.g. in all the IRE and the IRE+E and RE+E regions. The pulse can also be designed to eliminate electric discharge from the electrodes. The shape of the pulse can be optimized for the desired effect. For example, during conventional pulsed square electroporation, the start of the pulse may initiate the permeabilization of the cell membrane. However, the subsequent pulses while aiding to the cell membrane permeabilization may also produce substantial electrolytic products which after some number of pulses may produce a layer of gas around the electrodes. If the voltage of the electroporation pulses is sufficiently high and the gas layer is thin (as it may always be when the process starts), an ionization process of the gas occurs. This generates an electrical discharge across the ionized gas layer, associated with high pressure waves. However, if a decaying pulse is used for electroporation, this pulse has the ability to retain and even enlarge the permeabilizing pores. However, since the voltage decays, even when an electrolytically produced gas layer forms around the electrodes the voltage at that time may be low enough to avoid the production of sparks. An example numerical value for electric fields that develop across a gas layer to generate an electric breakdown and the consequent sparks may be approximately 30 kV/cm. Therefore, as long as the relation between the rate of production of electrolytic compounds and the gas layer and the voltage at the electrodes is lower than this value, there may continue to be electroporation and electrolysis without an electrical discharge across the gas layer.

In some embodiments the combination electrolysis and permeabilization may be combined with other modalities for tissue treatment such as thermal ablation, radiation, chemical ablation, and/or gene therapy.

FIGS. 2A and 2B are flow charts illustrating methods 200A, 200B according to embodiments of the disclosure. In some embodiments, a multimodality electrolysis system, device, and/or apparatus may be placed for treatment of a target site, for example, a tissue. The multimodality electrolysis system such as the system 100 illustrated in FIG. 1 may be used. The E2 treatments performed by the multimodality electrolysis system may be manually controlled by a user or may be controlled by a controller, for example, controller 105 shown in FIG. 1.

FIG. 2A illustrates a method of a generating a pulse, for example, the pulse illustrated in FIG. 1B, according to an embodiment of the disclosure. At Block 205, an initial voltage may be applied. The initial voltage may be applied to a treatment site with an electrode by transmitting an electrical signal to the electrode with a controller. The controller may be controller 105 shown in FIG. 1 in some embodiments. The initial voltage may be chosen to be sufficient to induce electroporation at the treatment site. In some embodiments, the current across the treatment site may be monitored, for example, by an electric meter such as electric meter 130 shown in FIG. 1. Once electroporation has occurred, the electric meter may detect changes in current as cellular permeabilization occurs. For example, the current may increase during permeabilization. The electric meter may also or alternatively detect changes in current as a gas layer accumulates due to formation of electrolytic products. For example, after the initial current increase after permeabilization, the electric meter may detect a decrease in current as the gas layer accumulates at the treatment site. The electric meter may provide the detected current as a current measurement to the controller. At Block 210, the voltage may be adjusted based on the current. The controller may transmit a signal to the electrode to reduce the voltage applied to the treatment site responsive to the detected current. The controller may maintain the reduced voltage or decay the voltage based on the desired width of the pulse. In some embodiments, a pH meter may monitor the pH of the treatment site. For example, the pH meter 125 shown in FIG. 1. The pH meter may transmit the detected pH at the treatment site to the controller. At Block 215, the voltage may be adjusted based on the pH. The controller may adjust the decaying voltage of the treatment pulse based, at least in part, on the detected pH. For example, the controller may adjust the decay of the voltage applied to the treatment site to maintain a desired pH for a desired amount of time. In another example, the controller may adjust the decay of the voltage applied to the treatment site so that the voltage level is maintained until a desired pH at the detection site is reached. The maintained voltage may be kept below the voltage required to induce sparking. The method described in FIG. 2A may produce a single pulse that may be adjusted based on the detected parameters.

In some embodiments, only Block 210 or Block 215 may be present. In some embodiments, Block 210 and 215 may be performed simultaneously. In some embodiments, the order of Blocks 210 and 215 may be reversed. In some embodiments, the voltage may be adjusted based on other parameters. For example, an imaging modality may transmit a signal to the controller when a color change associated with treatment is detected.

FIG. 2B illustrates a method 200B of a generating a pulse, for example, the pulse illustrated in FIG. 1C, according to an embodiment of the disclosure. A capacitance may be charged to an initial charge at Block 220. The capacitance may be charged responsive to a signal from a controller. The controller may be controller 105 shown in FIG. 1 in some embodiments. The charge in the capacitor may be discharged to apply a voltage at Block 225. An initial voltage may be applied to a treatment site with an electrode by transmitting an electrical signal to the electrode with the controller and/or coupling the electrode to the capacitance with the controller. The initial voltage may be chosen to be sufficient to induce electroporation at the treatment site. The initial voltage may then decay. Other than initiating the application of the pulse to the treatment site, the controller may not further alter shape of the pulse in some embodiments. In some embodiments, the electrical signal may be provided by a resistance and a capacitance coupled to a power supply. The capacitance and resistance may be selected to provide the desired initial voltage and time constant for the decay of the voltage pulse. The power supply may charge the capacitance, and responsive to the electrical signal of the controller, the capacitance may discharge through the resistance and the electrode to apply the pulse to the treatment site.

Other methods other than those described in methods 200A-B may be used to generate a single pulse to apply to a treatment site. For example, a function generator may be coupled to the electrode. The function generator may be coupled to the controller or controlled manually by a user.

In some embodiments, electrolysis and cellular permeabilization may be performed at the same time or partially at the same time. For example, current to generate electrolysis products may be provided during a same period of time as an electric field for electroporation, or current as a thermal source for permeabilizing cell membranes is applied to the tissue. In some embodiments, electrolysis and cellular permeabilization may both be performed together for a continuous period of time or intermittently. A pulse of current and/or voltage may be designed to cause the combination of electroporation and electrolysis that is desired in some examples. For example a continuous single pulse can be applied to deliver concurrently electrolysis and electroporation. The single pulse may be of a variety of different shapes, including but not limited to an exponential decay, a square wave, a triangle wave and wave with a rising leading edge or falling trailing edge. The single continuous pulse eliminates disruption of generation of electrolytic species that occurs with multiple pulse delivery configurations.

In some embodiments, the single pulse is delivered at the range sufficient to cause irreversible electroporation but not sufficient to cause any significantly contributing electrolytic species production that may cause electric discharge across the electrolytically produced gas layer. This configuration allows for tissue ablation in the non-electrolytic irreversible electroporation domain.

In some embodiments, one treatment may be performed continuously while the other treatment is performed intermittently. The magnitude and duration of each treatment may be modulated independently of the other treatment. For example, electrolysis may be performed continuously for several minutes while cellular permeabilization may be performed for several seconds each minute. The electrolysis may be discontinued while the cellular permeabilization continues to be performed. Other combinations of treatments may be possible. The time, duration, and order of the treatments may be chosen based at least in part on the desired effect on the target site, the size of the target site, and/or local physiological conditions of the target site.

In some embodiments, electrodes may be included on and/or in a treatment probe which may produce one of or both electrolysis and electroporation treatment. For example, the treatment probe may be used to execute the methods described above and/or illustrated in FIGS. 2A-B. In some embodiments, the treatment probe may be used to implement an electrolysis device and/or an electroporation device, such as devices 110, 115 illustrated in FIG. 1. In some embodiments, the treatment probe may be a combination device used to implement both devices 110, 115. The treatment probe may be implemented using a needle, a wire, a disk, and/or combinations thereof. In some embodiments, the electrode or electrodes may include the entire treatment probe. In some embodiments, the electrode or electrodes may be included as a portion of the treatment probe.

Figure 3:
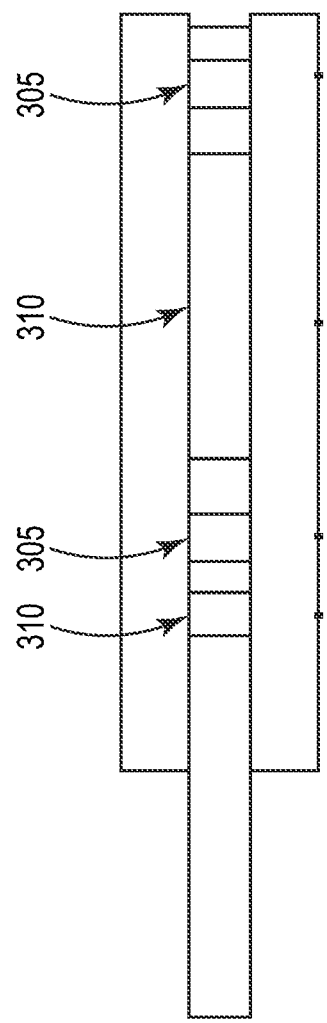
FIG. 3 is a schematic diagram of a treatment probe according to an embodiment of the disclosure.

FIG. 3 is a schematic diagram of a treatment probe 300 according to an embodiment of the disclosure. The treatment probe 300 may incorporate both electroporation electrodes 305 and electrolysis electrodes 310. The electrodes for electroporation 305 may be separate from the electrodes for electrolysis 310. Having separate electrodes for each treatment modality may allow for independent optimization of the electrode configuration for both electroporation and electrolysis. For example, the electrode design for electrolysis may include materials that are selected for specific electrolysis product species production. In some embodiments, the electroporation electrodes 305 and the electrolysis electrodes 310 may be combined into electrodes that perform both electrolysis and electroporation. The electrode material for electroporation may be selected to avoid electrolysis product formation from the electrodes that may introduce metals in the body systemically. For example through the use of Titanium electrodes. The electrodes may be in any number, size and shape of electrodes using a separate electrode delivery approach.

Figure 4:
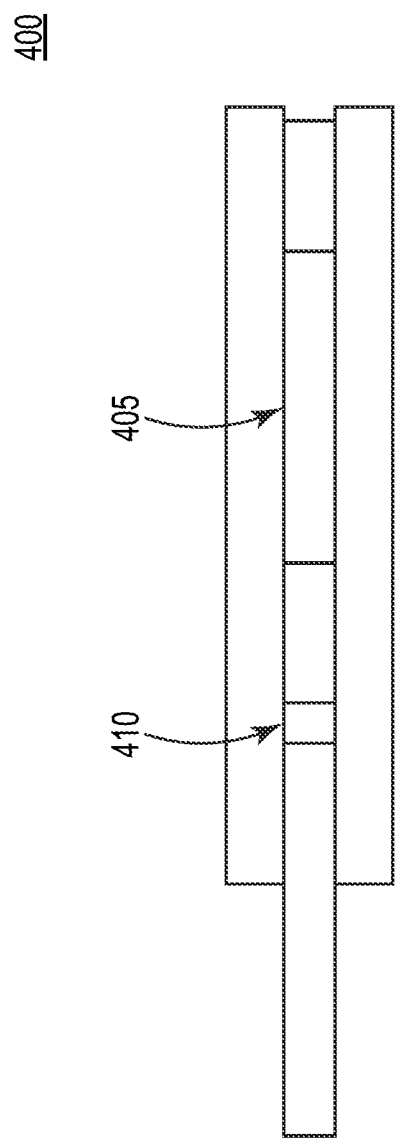
FIG. 4 is a schematic diagram of a treatment probe according to an embodiment of the disclosure.

FIG. 4 is a schematic diagram of a treatment probe 400 according to an embodiment of the disclosure. In some embodiments, a treatment probe may integrate the electrodes 405, 410 for electrolysis and electroporation. The electrodes for electrolysis, or certain ones of the electrodes, may be the same electrodes, or certain ones of the electrodes, that deliver electroporation. The electrodes may be in any number, size and shape using an integrated electrode approach. A number of different configurations may be used to integrate the delivery of electroporation and electrolysis into a catheter. The size, shape and configuration of the electrodes may be specifically tailored to the targeted treatment site.

In some embodiments, a treatment probe may include a combination of electrodes used for both electrolysis and electroporation delivery. For example, an electrode may be used for both electroporation and electrolysis. A separate electrode may be used to complete the electroporation delivery and a separate electrode may be used to complete the electrolysis delivery. In some embodiments, the electrodes may be included on a plurality of treatment probes. For example, a first probe may include the electrolysis anode and a second probe may include the electrolysis cathode. The first and second probes may further include electroporation electrodes. Other examples of electrode combinations include, but are not limited to, two point electrodes, one point and one needle electrode, one point electrode and one pad electrode, two monopolar needle electrodes; one bipolar needle, one multipolar needle; two surface electrodes; one surface and one needle electrode, and/or combinations thereof. Other configurations of electrodes on one or more treatment probes may also be possible. The spacing between electrodes on the treatment probe and/or the spacing between treatment probes may also be adjusted to achieve a desired electrolysis and/or electroporation effect.

Figure 5B:
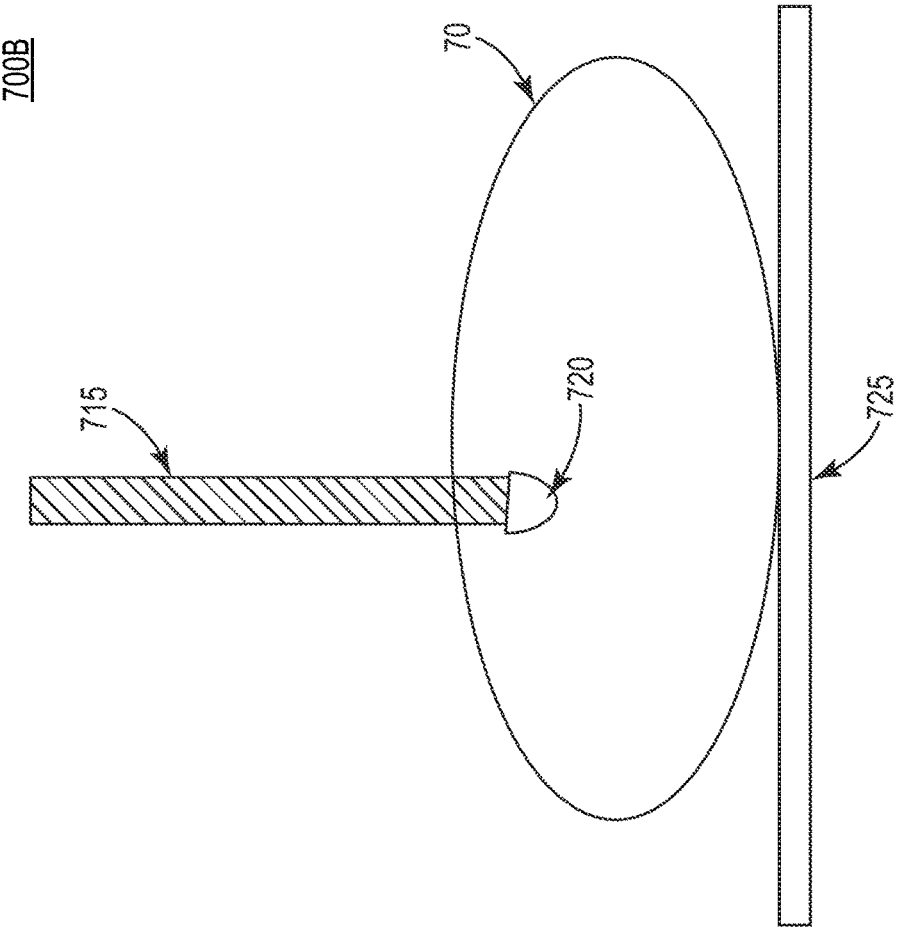
FIG. 5B illustrates an electrode configuration according to an embodiments of the disclosure.
Figure 5A:
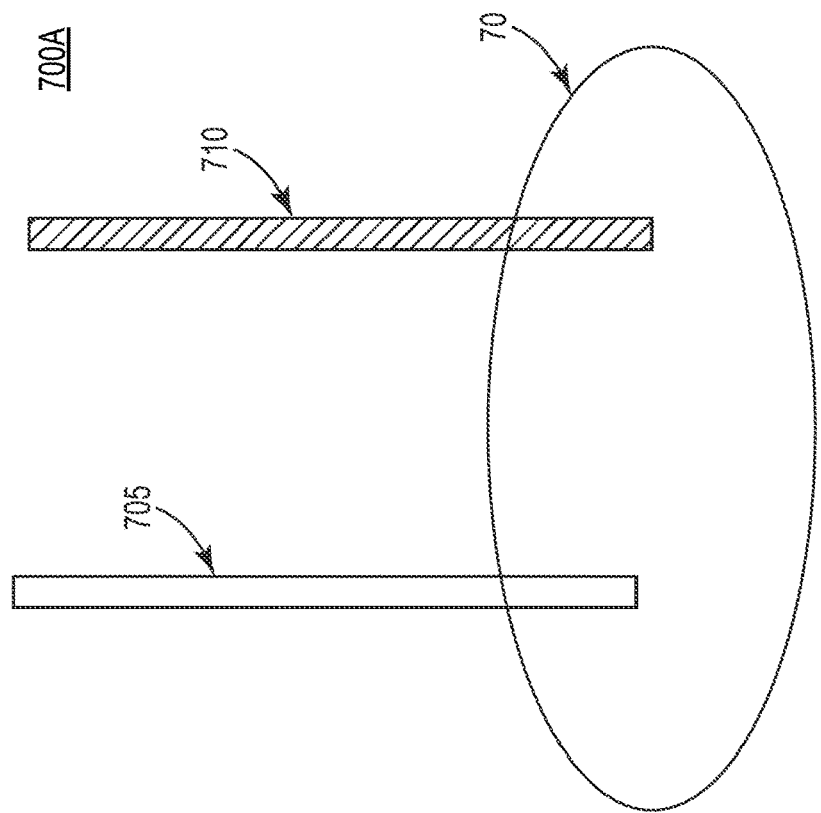
FIG. 5A illustrates an electrode configurations according to an embodiment of the disclosure.

FIGS. 5A-B illustrate two examples of electrode configurations 700A-B according to embodiments of the disclosure. FIG. 5A illustrates two needle electrodes 705, 710 inserted in a tissue 70. FIG. 5B illustrates a point electrode 720 on an insulated shaft 715 inserted in a tissue 70. A pad electrode 725 is placed remotely from the point electrode 720. In some embodiments, the point electrode 720 may be an anode and the pad electrode 725 may be a cathode. The examples shown in FIG. 5A-B are for illustrative purposes only, and other electrode configurations are possible.

The materials chosen for the electrodes, including the electrodes 705, 710, may be chosen to produce certain the electrolysis products. For example, an anode may include iridium oxide and/or rubidium oxide deposited on titanium, which may improve the production of hypochlorous acid, and a cathode may include copper. The use of mixed metal oxide anode electrodes may produce different species of electrolysis products that may be tailored for different clinical needs. For example, platinum may be used if inert electrodes are desired. Electroporation electrodes may include the same or different materials as electrolysis electrodes.

In some embodiments, a solution may be injected in tissue to affect the process of electrolysis. For instance a solution of buffered physiological saline at a pH of between 2 and 5 may preferentially produce electrolysis products, such as hypochlorous acid. The apparatuses, devices, and systems, such as treatment probes, may all be used to deliver E2. Other configurations, apparatuses, devices, and/or systems for delivering E2 may also be used. For example, one or more needle electrodes may be used in combination with an ultrasound transducer configured to provide sonoporation. Imaging of E2 could also employ computed tomography (CT), magnetic resonance imaging (MRI) and electrical impedance tomography. E2 treatment may also be combined with cryotherapy, thermal therapy, chemical therapy, and/or combinations thereof. For example a cryosurgery probe may also serve as one of the electrolysis electrodes.

Many clinical applications may benefit from the use of the combination of E2. The reduced energy requirement and reduce treatment times may overcome limitations that previously discouraged the use of either electroporation or electrolysis regardless of the benefits of each on a stand-alone basis. The combination of both may overcome the limitations and enable a multitude of clinical uses.

The treatment of a variety of cancers by the combination of electroporation and electrolysis may be an enhanced treatment approach. The targeted treatment site may be accessed minimally invasively by either catheter or probe placement. The configuration of the device and the electrodes may deliver the combination of electroporation and electrolysis in an optimal manner for the targeted tumor. The types of tumors may include but are not limited to prostate, breast, lung, liver, brain, colon, esophagus, kidney, rectal, skin, stomach, pancreas, eye and uterine tumors.

The combination of electroporation and electrolysis, E2, may be an effective clinical approach for both malignant and benign tumor treatments. Thus benign tumor sites like Benign Prostatic Hypertrophy, fibroids and myomas may be treated.

The E2 protocol may also be used to selectively ablate small volumes of tissue in the body such as a lymph node or a cluster of lymph nodes.

Another embodiment may utilize a method to control the dose the amount of electrolysis product produced and applied to the treatment site. A delivery device may be used to apply the electrolysis product produced at the time of application.

Some specific experimental examples are provided below to facilitate appreciation of embodiments described herein. The experimental examples presented are not intended to be comprehensive or exhaustive of all experiments performed or of all results obtained.

Example I

According to a first non-limiting example, a Petri dish was used to cast an agar gel made of physiological saline with a pH dye. The pH dye was 5% pH indicator (RC Hagen wide range). The pH indicator was added to the agar gel phantom before its solidification. Two 0.9 mm graphite electrodes were inserted into the gel through a holder. Graphite was used to avoid contamination of the gel with metal ions. The electrodes were connected to a constant voltage power supply or to a BTX electroporation (Harvard Instruments) electroporator. The distance between the electrodes was 10 mm. Changes in color near the electrodes were observed due to electrolysis induced change in pH.

The first experiment involved the delivery of typical electroporation pulses of 1000 V between the electrodes. One hundred microsecond long pulses at a frequency of 1 Hz in groups of 99 pulses were delivered. Between groups of pulses, a two minute rest period was used to let the system cool.

The gel exhibited a stained region after 99 pulses. The stained region surrounded the electrodes and was not continuous, confirming the delivery of electrolysis products. However, the extent of the stain did not cover the treated tissue to the isoelectric field of 200 Vcm or 100 V/cm line, produced by the 1000 V electroporation pulses. In typical irreversible electroporation protocols used in current clinical applications, fewer than 100 pulses are used. Under these typical conditions there are no electrolysis products in the region of electric fields of 100 V/cm or 200 V/cm. 200 V/cm and 100 V/cm are reversible electroporation fields that do not cause cell death in the absence of electrolytic products.

After three sequences of 99 pulses, a substantial volume of gel in the treated region has been affected by the products of electrolysis and has changed the pH of the gel. However, even after 3×99 pulses, the region affected by electrolysis has not yet reached the 100 V/cm isoelectric field line. The region affected by the anode was larger than that affected by the cathode. In addition, in the center of the region stained near the anode there was a white discolored circle. This may be due to a typical effect of electrolysis. In electrolysis there is an electro-osmotic driven flow of water from the anode to the cathode. This is a well-known phenomenon. This phenomenon may be used to generate flows in tissue during electrolysis in desirable directions. Furthermore, by adding electrolysis products by extending electrolysis treatment and/or introducing a solution configured for electrolysis product production, the treated zone may be substantially expanded.

Example II

According to a second non-limiting example, a Petri dish was used to cast an agar gel made of physiological saline with a pH dye. The pH dye was 5% pH indicator (RC Hagen wide range). The pH indicator was added to the agar gel phantom before its solidification. Two 0.9 mm graphite electrodes were inserted into the gel through a holder. Graphite was used to avoid contamination of the gel with metal ions. The electrodes were connected to a constant voltage power supply or to a BTX electroporation (Harvard Instruments) electroporator. The distance between the electrodes was 10 mm. Changes in color near the electrodes were observed due to electrolysis induced change in pH.

The second experiment involved the delivery of typical electroporation pulses of 500 V between the electrodes. One hundred microsecond long pulses at a frequency of 1 Hz in groups of 99 pulses were delivered. Between groups of pulses, a two minute rest period was used to let the system cool.

The pH affected area after three pulse sequences of 99 pulses and a voltage between electrodes of 500 V is smaller than when the pulse was of 1000 V.

Example III

According to a third non-limiting example, a Petri dish was used to cast an agar gel made of physiological saline with a pH dye. The pH dye was 5% pH indicator (RC Hagen wide range). The pH indicator was added to the agar gel phantom before its solidification. Two 0.9 mm graphite electrodes were inserted into the gel through a holder. Graphite was used to avoid contamination of the gel with metal ions. The electrodes were connected to a constant voltage power supply or to a BTX electroporation (Harvard Instruments) electroporator. The distance between the electrodes was 10 mm.

The DC power supply applied a voltage of 10 V (a current of 60 mA) between the electrodes. It was evident that after 168 seconds the pH dye area marked as affected by electrolysis products from direct current was much larger than the area affected by electrolysis products generated by electroporation pulses in Examples I and II. The pH change affected area was sufficiently large so that a 1000 V pulse applied between the electrodes may ablate to the isoelectric field line of 100 V/cm. 100 V/cm is considered reversible electroporation and permeabilization of the cell membrane is typically done with eight pulses. Cells survive exposure to electric fields of eight, 100 V/cm. However, when electrolytic products are generated in sufficient quantity to diffuse to the 100 V/cm isoelectric-field lines, the cells exposed to eight 100 V/cm electric fields do not survive. Therefore, it appeared that a preferential way to use the combination of electrolysis/electroporation for tissue ablation is to use conventional electrolysis with relatively (compared to electroporation) long DC currents at low voltage and current for the products of electrolysis to diffuse through the targeted volume in combination with several high field electroporation type pulses that are sufficient to permeabilize the cell membrane. There may be several possible combination protocols with electrolysis type currents and electroporation type pulses delivered in various sequences and configurations. For instance: electrolysis first, electroporation later or electroporation first electrolysis later, or at different intervals in time between electrolysis and electroporation.

Example IV

According to a fourth non-limiting example, a Petri dish was used to cast an agar gel made of physiological saline with a pH dye. The pH dye was 5% pH indicator (RC Hagen wide range). The pH indicator was added to the agar gel phantom before its solidification. Two 0.9 mm graphite electrodes were inserted into the gel through a holder. Graphite was used to avoid contamination of the gel with metal ions. The electrodes were connected to a constant voltage power supply or to a BTX electroporation (Harvard Instruments) electroporator. The distance between the electrodes was 10 mm.

A voltage of 5 V was applied across the electrodes with a current of 9 mA. Staining indicated that this produced a comparable outcome to electrolytic treatment with 10 V in Example III and is also suitable for tissue electrolysis/electroporation ablation protocol described in Example III. The center of the stained gel near the anode was discolored because of the water electromigration effect.

Example V

Conventional tissue ablation by electroporation is delivered using two electrodes, relatively close to each other to facilitate high electric fields with reasonable high voltages. It may be advantageous to ablate tissue by electroporation in a modality similar to radio-frequency thermal ablation, i.e. one electrode in the center of the undesirable tissue and a second electrode remotely. However, a problem with this configuration may be that for a single needle or point active electrodes with a remote second electrode, the electric field near the needle or point electrode descends very rapidly with distance from the electrode. In the case of the needle electrode, as one over the distance square and in the case of a point electrode, as one over the distance to the third power.

According to a fifth, non-limiting example, a typical one dimensional in cylindrical coordinates needle electrode was used. The central electrode was 0.9 mm graphite and the second electrode was a lining of copper around the wall of a Petri dish. The Petri dish was used to cast an agar gel made of physiological saline with a pH dye. The pH dye was 5% pH indicator (RC Hagen wide range). The pH indicator was added to the agar gel phantom before its solidification.

A sequence of electrolysis/electroporation treatment was applied with a single needle with 10 V and 200 mA. Two sets of experiments were performed, one set with the anode in the center and one set with the cathode in the center. The gel was observed after 45 seconds, 90 seconds, 120 seconds after start of electrolysis. Staining was observed around the electrode in both sets of experiments after 45 seconds, and the stained area continued to increase as time went on. The amount of electrolysis products observed in this set of experiments was significantly higher than for the case of two adjacent electrodes at the same voltage in the previous examples. The reason may be that the current was higher and/or possibly because the products from the anode and cathode do not interact with each other due to the increased distance. These experiments suggest that it may be advantageous to generate the electrolysis products from a central electrode with a distant second electrode. First the amount of electrolysis products appears to be higher and the composition appears to be better defined. It may be preferable when two electrodes are used for electroporation to use one or both of these electrodes with one polarity and another remote electrode with another polarity for generating electrolysis products in some applications. Second, this configuration of a central cylindrical or point electrode may take the most advantage of the combination of electrolysis and electroporation, because of the nature of the electric field distribution.

Example VI

According to a sixth non-limiting example, a typical one dimensional in cylindrical coordinates needle electrode was used. The central electrode was 0.9 mm graphite and the second electrode was a lining of copper around the wall of a Petri dish. The Petri dish was used to cast an agar gel made of physiological saline with a pH dye. The pH dye was 5% pH indicator (RC Hagen wide range). The pH indicator was added to the agar gel phantom before its solidification. Three sets of 1000 V, 100 microsecond long 1 Hz frequency, 99 pulses per set were delivered between the central electrode and the electrode around the Petri dish.

It was observed that at a delivery time of 5 minutes with 1000 V electroporation type pulses, a negligible amount of electrolysis products relative to those produced by DC electrolysis in the previous examples. The isoelectric field lines typical of reversible electroporation were much closer to the central electrode than the isoelectric lines of 100 V/cm From the central electrode Examples V and VI, it is observed that combining electrolysis with electroporation may substantially expand the region of tissue ablation over electroporation alone. However, this may require that the extent of electrolytic effects be properly designed in relation to the extent of the electric fields generated. The various combinations of electrolysis and electroporation sequences discussed earlier may be valid here also.

Example VII

According to a seventh, non-limiting example, a standard electroporation system, ECM 830 electroporator, (BTX, San Diego, Calif.) with a typical electroporation 2 mm cuvette, 620 BTX was used. Specifically, 2 mm cuvettes were filled with pH buffered saline with an initial pH of 7.5 with cells, and applied electroporation protocols. Changes in pH were measured immediately after the delivery of the electroporation pulse sequences using an Oakton Instruments (PH 450) meter (Vermonth Hills, Ill.) with a micro-combination pH probe MI-414B (16 gauge, tip 6 cm length) (Bedford, N.H.) pH probe. The results are shown in the table in FIG. 6. The pH data is the average pH from three repeats and the standard deviation. The pH was measured at the end of the electroporation field delivery protocol and represents the pH that would have existed when the cells were removed from the cuvettes for viability processing in. The table in FIG. 6 shows that the pH has changed in all the experiments and has become basic, which suggests the presence of electrolytic products. The difference in time of exposure to products of electrolysis during electroporation and the charge seem to correlate to cell viability.

Example VIII

According to an eighth, non-limiting example, pig liver tissue was ablated between two titanium electrodes 1.5 cm apart. In a first experiment, a first single exponential decay pulse was applied. The pulse had an initial voltage of 1230 V and a decay time constant of 2.4 ms. A square pulse was then applied for 10 minutes with a current of 200 mA. The square pulse was followed by a second exponential decay pulse having an initial voltage of 1160 V and a time constant of 2 ms.

In a second experiment, an initial exponential decay pulse was applied with an initial voltage of 1260 V and a time constant of 2.6 ms. After the exponential decay pulse, a square pulse was applied for 5 minutes with a current of 100 mA. The square pulse was followed by a second exponential decay pulse having an initial voltage of 1210 V and a time constant of 2.2 ms.

Both experiments demonstrated tissue ablation in the pig liver.

Example IX

According to a ninth, non-limiting example, pig liver tissue was ablated between two titanium electrodes 5 cm apart. A single exponential decay pulse was applied. The pulse had an initial voltage of 1040 V and a time constant of 2.2 ms. The experiment demonstrated complete tissue ablation in the pig liver between the electrodes.

The examples provided are for explanatory purposes only and should not be considered to limit the scope of the disclosure.

Those skilled in the art will recognize that the examples provided of both the design delivery systems and the clinical applications are not the limit of the uses of the combination of electroporation and electrolysis. Many configurations of delivery systems exist, as well as applications that would benefit from the use of the discovery we disclose.

It is to be appreciated that any one of the above embodiments or processes may be combined with one or more other embodiments and/or processes or be separated and/or performed amongst separate devices or device portions in accordance with the present systems, devices and methods.

Finally, the above-discussion is intended to be merely illustrative of the present devices, apparatuses, systems, and methods and should not be construed as limiting the appended claims to any particular embodiment or group of embodiments. Thus, while the present disclosure has been described in particular detail with reference to exemplary embodiments, it should also be appreciated that numerous modifications and alternative embodiments may be devised by those having ordinary skill in the art without departing from the broader and intended spirit and scope of the present disclosure as set forth in the claims that follow. Accordingly, the specification and drawings are to be regarded in an illustrative manner and are not intended to limit the scope of the appended claims.

What is claimed is:

1. An apparatus for tissue ablation, the apparatus comprising:
   an electrode configured to provide a pulse of a voltage or a current to a treatment site; and
   a controller coupled to the electrode, the controller configured to provide an electronic signal to the electrode, wherein the electronic signal determines a rising edge, a plateau, and a falling edge of the pulse,
   wherein the rising edge, the plateau, and the falling edge of the pulse are configured by the controller to induce at least one of electrolysis and electroporation at the treatment site, and
   wherein a width of the plateau is configured by the controller such that an electric field near the electrode is less than an ionization field of a gas at the treatment site.

2. The apparatus of claim 1, further comprising an electric meter configured to provide a current measurement from the treatment site to the controller, wherein the controller is further configured to adjust at least one of the rising edge, plateau, and falling edge of the pulse in response to the current measurement.

3. The apparatus of claim 1, further comprising a pH meter configured to provide a pH measurement from the treatment site to the controller, wherein the controller is further configured to adjust at least one of the rising edge, plateau, and falling edge of the pulse in response to the pH measurement.

4. The apparatus of claim 1, wherein at least one of the rising edge, plateau, and falling edge of the pulse are configured so that a majority of the tissue ablation is due to electroporation.

5. The apparatus of claim 1, wherein at least one of the rising edge, plateau, and falling edge of the pulse are configured so that a majority of the tissue ablation is due to electrolysis.

6. The apparatus of claim 1, wherein the electrode comprises titanium.

7. The apparatus of claim 1, wherein the treatment site is a lymph node.

8. The apparatus of claim 1, wherein the treatment site is a tumor.

9. The apparatus of claim 1, wherein the electroporation induced is reversible electroporation.

10. The apparatus of claim 1, wherein the electroporation induced is irreversible electroporation.

11. The apparatus of claim 1, wherein the falling edge comprises an exponential decay.

12. The apparatus of claim 1, wherein the current s a direct current.

* * * * *